United States Patent
McMinn et al.

(10) Patent No.: US 6,797,849 B2
(45) Date of Patent: Sep. 28, 2004

(54) XYLENE ISOMERIZATION

(75) Inventors: Timothy E. McMinn, Houston, TX (US); Gary David Mohr, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 56 days.

(21) Appl. No.: 10/285,851

(22) Filed: Nov. 1, 2002

(65) Prior Publication Data

US 2004/0087823 A1 May 6, 2004

(51) Int. Cl.[7] ................................................. C07C 5/27
(52) U.S. Cl. ..................... 585/319; 585/477; 585/480; 585/481
(58) Field of Search ............................... 585/304, 314, 585/300, 477, 480, 481, 482

(56) References Cited

U.S. PATENT DOCUMENTS 5,015,794 A  *  5/1991  Reichmann ................. 585/258
5,030,788 A  *  7/1991  Amelse et al. .............. 585/480
5,977,420 A  * 11/1999  Abichandani et al. ....... 585/319

* cited by examiner

Primary Examiner—Thuan Dinh Dang

(57) ABSTRACT

A process for isomerizing xylenes in a feed containing xylenes is disclosed which process comprises: contacting the feed with a first isomerization catalyst in a first reactor under a first set of conditions effective to isomerize xylenes in the feed; and contacting the xylenes with a second isomerization catalyst in a second reactor under a second set of conditions effective to isomerize xylenes in the feed. The second reactor is typically a clay treater and contains a further catalyst effective under the second set of conditions to remove olefins in the feed. Any ethylbenzene in the feed is removed, either by dealkylation or isomerization, in the first reactor or in a third reactor upstream of the first and second reactors.

27 Claims, 1 Drawing Sheet

XYLENE ISOMERIZATION

FIELD

This invention is directed to a xylene isomerization process.

BACKGROUND

Para-xylene is a valuable chemical feedstock which may be derived from mixtures of $C_8$ aromatics separated from such raw materials as petroleum naphthas, particularly reformates, usually by selective solvent extraction. The $C_8$ aromatic fractions from these sources vary quite widely in composition but will usually contain 10 to 32 wt. % ethylbenzene (EB) with the balance, xylenes, being divided between approximately 50 wt. % meta and 25 wt. % each of para and ortho.

Individual isomer products may be separated from the naturally occurring mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization or selective adsorption (e.g., the Parex process).

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability to convert ethylbenzene in the feed to useful products while simultaneously minimizing any conversion of xylenes to other compounds.

One known method for removing ethylbenzene from a $C_8$ aromatic stream is by dealkylation in which the ethylbenzene is converted to benzene and ethylene, with the latter normally being hydrogenated to produce ethane. Another known method for removing ethylbenzene is by isomerization to produce additional xylenes, normally through the intermediate step of saturating the ethylbenzene to produce naphthenes. In the past, a single catalyst was used to effect both xylene isomerization and ethylbenzene conversion, but this necessarily involved compromising between the different catalytic requirements of the two reactions. More recently, processes have been developed which employ separate catalysts tailored specifically for the different catalytic functions.

For example, U.S. Pat. No. 4,899,011 describes a xylene isomerization process employing ethylbenzene dealkylation, in which a $C_8$ aromatic feed, which has been depleted in its para-xylene content, is contacted with a two component catalyst system. The first catalyst component selectively converts the ethylbenzene by deethylation, while the second component selectively isomerizes the xylenes to increase the para-xylene content to a value at or approaching the thermal equilibrium value. The first catalyst component comprises a Constraint Index 1–12 molecular sieve, such as ZSM-5, which has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury, whereas the second component comprises a Constraint Index 1–12 molecular sieve which has an ortho-xylene sorption time of less than 10 minutes under the same conditions. In one preferred embodiment, the first catalyst component is ZSM-5 having a crystal size of at least 1 micron and the second catalyst component is ZSM-5 having a crystal size of 0.02–0.05 micron. Each catalyst component also contains a hydrogenation component, preferably a platinum group metal.

An improvement over the process of U.S. Pat. No. 4,899,011 is described in U.S. Pat. No. 5,689,027 in which the first catalyst component in the two component system is preselectivated by coking, or more preferably by deposition of a surface coating of silica, to increase its ortho-xylene sorption time to greater than 1200 minutes under the same conditions as cited in the '011 patent. Using such a system it is found that high ethylbenzene dealkylation rates can be achieved with significantly lower xylene losses than obtained with the process of the '011 patent.

Although the first and second catalyst components of the systems described in U.S. Pat. Nos. 4,899,011 and 5,689,027 can be housed in separate reactors, these processes are usually practiced in a single reactor in which the different components form separate beds in, for example, a fixed, stacked bed reactor. In contrast, U.S. Pat. No. 5,705,726 describes a similar process in which the ethylbenzene dealkylation step is performed in a separate reactor from that used for the subsequent xylene isomerization step. In theory, such a two reactor system offers significant advantages over a stacked bed system in that it allows the operating conditions as well as the catalyst properties to be tailored for the different reactions involved. In this way, it should be possible to operate at high ethylbenzene conversion while the xylene isomerization step is conducted at the milder conditions necessary to minimize reduce xylene losses. In practice, however, two reactor systems have generally not been adopted at least in part because of the increased capital cost of installing a second reactor and associated equipment.

U.S. patent application Ser. No. 10/138,223, filed May 2, 2002, describes a process which allows xylene isomerization and ethylbenzene conversion to be conducted in separate reactors without significant increase in capital cost by utilizing space within an existing reactor, i.e., a clay treater, to accommodate the xylene isomerization catalyst. In particular, that invention is based on the realization that the product from the xylene isomerization step is normally fed to a clay treater to effect removal of any trace olefins in the product and that recent advances in olefin removal catalysts have significantly reduced the amount of catalyst required in the clay treater. As a result the clay treater provides reactor space which is already available in a conventional aromatics plant and which is suitable for accommodating a xylene isomerization catalyst. In addition, since the clay treater is operated at mild conditions compared with those employed in conventional xylene isomerization processes, the xylene losses can be reduced to very low levels.

It is known that the equilibrium levels of para-xylene/xylenes are higher at lower temperatures and that typical clay treaters operate between about 150 to 230° C. (300° to 450° F.) while typical ethylbenzene dealkylation-based isomerization units operate between about 410 to 450° C. (775° to 840° F.). If equilibrium could be reached at the lower temperatures, the amount of para-xylene in the xylenes would increase by about 0.8–1.2%. The present invention seeks to provide a process for increasing the content of para-xylene at those lower temperatures.

SUMMARY

In one aspect, the invention resides in a process for isomerizing xylenes in a feed containing xylenes, which process comprises:

contacting the feed with a first isomerization catalyst contained in a first reactor under a first set of conditions effective to isomerize xylenes in the feed; and contacting the feed with a second isomerization catalyst contained in a second reactor under a second set of conditions effective to isomerize xylenes in the feed, the second reactor being separate from the first reactor and containing a further catalyst effective under said second set of conditions to remove olefins in the feed.

Conveniently, said second set of conditions are different from, and typically include a lower temperature than, said first set of conditions In one embodiment, contacting the feed with the first isomerization catalyst occurs before contacting the feed with the second isomerization catalyst.

In an alternative embodiment, contacting the feed with the first isomerization catalyst occurs after contacting the feed with the second isomerization catalyst.

In a further aspect, the invention resides in a process for isomerizing xylenes in a feed which contains ethylbenzene and xylene, which process comprises the steps of:

contacting the feed with an ethylbenzene conversion catalyst under ethylbenzene conversion conditions, wherein the ethylbenzene conversion catalyst is effective under the ethylbenzene conversion conditions to convert ethylbenzene in the feed and produce an ethylbenzene-depleted product;

contacting the ethylbenzene-depleted product with a first xylene isomerization catalyst in a first reactor under a first set of conditions effective to isomerize xylenes in the feed to produce an isomerized product; and contacting the feed or the isomerized product with a second xylene isomerization catalyst in a third reactor under a second set of conditions effective to isomerize xylenes in the feed, the third reactor also containing a further catalyst effective under said second set of conditions to remove olefins in the feed.

DESCRIPTION OF THE EMBODIMENTS

The present invention provides process for isomerizing xylenes in a $C_8$ aromatics feedstock in which the feedstock is contacted with first and second xylene isomerization catalysts located respectively in first and second separate reactors. The first or main xylene isomerization catalyst is operated under conventional xylene isomerization conditions (typically about 410 to 450° C.), whereas the second or trim xylene isomerization catalyst is operated under the same conditions as (typically about 150 to 230° C.), and located in the same reactor as, the catalyst used to remove olefins from the feedstock. In an existing isomerization plant, this reactor would be the clay treater conventionally used for olefin removal from the isomerized product, either by replacement of the clay with a molecular sieve catalyst requiring significantly less catalyst volume or by filling available space in the clay treater. In a grass roots plant, the reactor could be designed to accommodate the xylene isomerization catalyst together with a clay and/or a molecular sieve olefin removal catalyst. It is also possible that a single catalyst could be used that would effectively remove olefins as well as effect xylene isomerization.

Normally, the $C_8$ aromatics feedstock will also contain ethylbenzene which is preferably removed, by conversion to other valuable products, to avoid downstream separation problems. The catalyst used to effect ethylbenzene conversion step is conveniently located in the first or main xylene isomerization reactor, for example by including therein separate beds of ethylbenzene conversion catalyst and first xylene isomerization catalyst. Alternatively, the ethylbenzene conversion catalyst can be located in a third reactor, separate from the first and second reactors.

Figure 1:
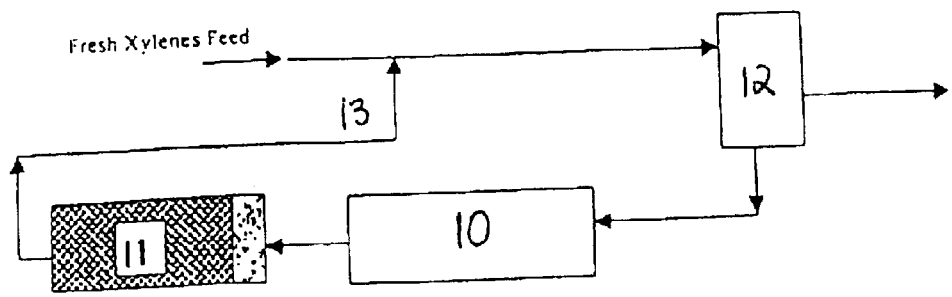
FIG. 1 is a flow diagram of a xylene isomerization process according to a first embodiment of the invention.

Referring to FIG. 1, in the first embodiment of the invention shown therein the first reactor 10 containing the first or main isomerization catalyst is located upstream of the second reactor 11. In this embodiment, the fresh xylenes feed is passed into a para-xylene recovery unit 12, such as a fractional crystallizer, where para-xylene product is recovered and the para-xylene-depleted feed is then passed to the first reactor 10. Assuming the process is being used to handle ethylbenzene-containing feeds, the reactor 10 will also normally contain a bed of ethylbenzene conversion catalyst located before the first isomerization catalyst. After passage through the first reactor 10, the feed flows to the second reactor 11, which contains the second or trim xylene isomerization catalyst and preferably a separate bed of an olefins removal catalyst, such as clay, located after the second isomerization catalyst. The effluent from the second reactor 11 is then recycled through line 13 to the para-xylene recovery unit 12. In this embodiment, since the xylenes in the feedstock entering the second reactor 11 are already close to equilibrium from passage through the first reactor 12, a relatively small amount of the second isomerization catalyst should be sufficient to re-equilibrate the xylenes at the lower temperature in the second reactor. In this way, an increase in the amount of para-xylene in the feedstock xylenes of the order of 0.8% should be possible.

Figure 2:
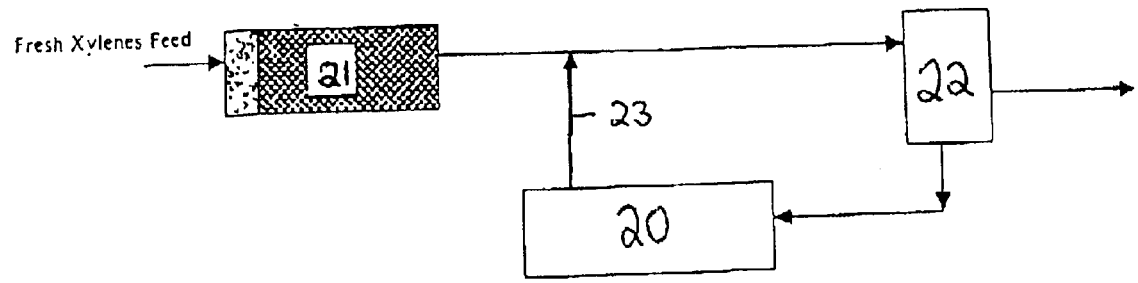
FIG. 2 is a flow diagram of a xylene isomerization process according to a second embodiment of the invention

Referring to FIG. 2, in the second embodiment of the invention the first reactor 20 containing the first or main isomerization catalyst is located downstream of the second reactor 21. In this embodiment, the fresh xylenes feed is fed directly to the second reactor 21 where it contacts a bed of the second or trim xylene isomerization catalyst and then preferably a separate bed of an olefins removal catalyst, such as clay. From the reactor 21, the feed is passed into a para-xylene recovery unit 22, such as a fractional crystallizer, where para-xylene product is recovered and the para-xylene-depleted feed is then passed to the first reactor 20, similar to the reactor 10 of the first embodiment. The effluent from the first reactor 20 is then recycled through line 23 to the para-xylene recovery unit 22. In this embodiment, since the fresh feed entering the xylene loop typically comes from a reformer and hence is at high temperature (of the order of 540° C.), passage through the second reactor, which typically operates at 150 to 230° C., should result in a more para-xylene favorable equilibrium before para-xylene separation in the recovery unit 22. In this way, an increase in the amount of para-xylene in the feedstock xylenes up to 1.2% should be possible.

In addition to providing a more para-xylene favorable equilibrium, the provision of the trim xylene isomerization catalyst allows additional para-xylene recovery when, for example, the operational severity of the first isomerization reactor is reduced in times of reduced throughput. Reducing operational severity is usually accomplished by lowering the temperature of the reactor, which reduces aging rates, xylene losses and approach to para-xylene equilibrium. Reduced aging rates and xylenes losses are desirable but reduced para-xylene equilibrium approach is not. Having a small quantity of isomerization catalyst in the second reactor (kept at constant temperature) would help make up some of the lost para-xylene. Although full equilibrium may not be achieved in the second reactor, it would still improve overall para-xylene yield.

In addition, the trim xylene isomerization catalyst provides additional para-xylene when the isomerization function of first catalyst has become deactivated. Thus, in some cases, the "end-of-run" for a xylene isomerization reactor may be dictated by a loss of para-xylene approach to equilibrium rather than a low ethylbenzene conversion activity. With extra isomerization activity in the second reactor, the usable lifetime of the first isomerization catalyst could be extended since overall para-xylene approach would be improved.

Feedstock

In general, any aromatic $C_8$ mixture containing xylene may be used as the feed to the process of this invention. Generally, such a mixture will typically have an ortho-xylene content in the approximate range of 0 to 35 weight percent, a meta-xylene content in the approximate range of 20 to 95 weight percent and a para-xylene range of 0 to 15 weight percent. In addition, the feed will also normally contain ethylbenzene, typically in an amount between about 5 to about 60 weight percent. The feed in addition to the above aromatic $C_8$ mixture may contain non-aromatic hydrocarbons, i.e., naphthenes and paraffins in an amount up to 30 weight percent. In a preferred embodiment, the invention provides means to process a mixture of $C_8$ aromatics such as that derived from catalytic reforming of a petroleum naphtha to a mixture of reduced ethylbenzene content and increased content of para-xylene. The invention is particularly effective in treating a para-xylene lean mixture of $C_8$ aromatics to increase the para-xylene concentration up to approximately the thermal equilibrium level.

Ethylbenzene Conversion Catalyst

If the $C_8$ aromatics feedstock contains a significant quantity of ethylbenzene, the feedstock is subjected to an ethylbenzene conversion step since separation of ethylbenzene from para-xylene is difficult. The ethylbenzene conversion step may be effected by contacting the feed with an ethylbenzene conversion catalyst in a reactor separate from, and upstream of, the first and second isomerization reactors. More preferably, however, the ethylbenzene conversion step is conducted in the first isomerization reactor by including in said reactor a separate bed of ethylbenzene conversion catalyst upstream of the first xylene isomerization catalyst.

In a first and preferred embodiment of the invention, the ethylbenzene conversion step is effected by deethylation to produce benzene and light gas (normally ethane). Suitable catalysts for converting ethylbenzene by deethylation include intermediate pore size molecular sieves, which typically have a pore size of about 5 to less than about 7 Angstroms and are generally characterized by having a Constraint Index within the approximate range of 1 to 12. The method by which Constraint Index is determined is described fully in U.S. Pat. No. 4,016,218, incorporated herein by reference for details of the method. Examples of intermediate pore size molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 and ZSM-58. The entire contents of the above references are incorporated by reference herein.

The molecular sieve employed in the dealkylation catalyst preferably has a relatively high acid activity, as measured by having an alpha value of at least 50, more typically of about 100 to about 500 and preferably of about 100 to about 300. The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The molecular sieve used in the ethylbenzene dealkylation catalyst is preferably associated with a hydrogenation-dehydrogenation component. Examples of such components include the oxide, hydroxide, sulfide, or free metal (i.e., zerovalent) forms of Group 8 metals (i.e., Pt, Pd, Ir, Rh, Os, Ru, Ni, Co and Fe), Group 6 metals (i.e, Cr, Mo, W), Group 14 metals (i.e., Sn and Pb), Group 15 metals (i.e., Sb and Bi), and Group 7 metals (i.e., Mn, To and Re). Combinations of catalytic forms of such noble or non-noble metals, such as combinations of Pt with Sn, may be used. The metal is preferably in a reduced valence state. The reduced valence state of the metal may be attained, in situ, during the course of the reaction, when a reducing agent, such as hydrogen, is included in the feed to the reaction.

In one preferred embodiment of the invention, the hydrogenation-dehydrogenation component is a noble metal (i.e., Pt, Pd, Ir, Rh, Os and Ru) and most preferably is platinum. In a further preferred embodiment of the invention, the hydrogenation-dehydrogenation component is an early transition metal, such as molybdenum, tungsten, rhenium and/or manganese, most preferably rhenium.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetraamineplatinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the molecular sieve. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(I) chloride. Anionic complexes such as the metatungstate, permanganate or perrhenate ions are also useful for impregnating metals onto the molecular sieves. After incorporation of the metal, the catalyst can then be filtered, washed with water and calcined at temperatures of from about 250 to about 500° C.

The amount of the hydrogenation-dehydrogenation component is suitably from about 0.001 to about 10 percent by weight, e.g., from about 0.1 to about 5 percent by weight, e.g., from about 0.1 to about 2 percent by weight, although this will, of course, vary with the nature of the component, with less of the highly active noble metals, particularly platinum, being required than of the less active base metals.

In addition, it may be desirable to combine the molecular sieve dealkylation catalyst with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

Improved results and, in particular reduced xylene losses, are obtained when the ethylbenzene dealkylation catalyst is arranged to have carefully controlled xylene diffusional properties. These properties can be identified by noting the time (in minutes) required for the catalyst to sorb 30% of its equilibrium capacity for ortho-xylene at 120° C. and at an ortho-xylene partial pressure of 4.5±0.8 mm of mercury, such a test being described in U.S. Pat. Nos. 4,117,026; 4,159,282; and Re. 31,782; each of which is incorporated by reference herein. In particular, the ethylbenzene dealkylation catalyst is preferably selected so as to have an ortho-xylene sorption time (in minutes) in excess of about 50 and preferably greater than about 1200, but less than 10,000.

The desired xylene diffusion properties of the ethylbenzene dealkylation catalyst component can be achieved in a number of ways. For ortho-xylene diffusion times at or near the minimum value of 50 minutes, the selection of a large crystal form of the molecular sieve used in the catalyst, that is, having an average crystal size in excess of 1 micron, may be sufficient. However, to achieve higher diffusivity values, it may be desirable to selectivate the first catalyst component by deposition on the surface of the catalyst particles of a layer of coke and/or an oxide, such as silica, which is inert under the process conditions experienced in use. Where the catalyst particles are selectivated, both large crystal size and medium crystal size (having a crystal size of 0.2–0.5 micron) molecular sieves can be used.

Where the ethylbenzene dealkylation catalyst component is to be selectivated with silica, this is conveniently achieved by subjecting the catalyst to one or more treatments with an organosilicon compound in a liquid carrier, each treatment being followed by calcination of the treated material in an oxygen-containing atmosphere, e.g., air. Such a multiple selectivation procedure is described in U.S. Pat. No. 5,476,823, the entire contents of which are incorporated herein by reference.

The organosilicon compound which is used to selectivate the first catalyst component may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferably, the kinetic diameter of the organosilicon compound, which is used to preselectivate the molecular sieve, is larger than the molecular sieve pore diameter, in order to avoid entry of the organosilicon compound into the molecular sieve pores and any concomitant reduction in the internal activity of the molecular sieve.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

Preferably, the liquid carrier for the organosilicon compound is an organic compound, such as a linear, branched or cyclic hydrocarbon having five or more, especially 7 or more, carbon atoms per molecule, e.g., an alkane, such as heptane, octane, nonane or undecane. The boiling point of the organic compound, e.g., alkane, may be greater than about 70° C. Mixtures of low volatility organic compounds, such as hydrocracker recycle oil, may be employed as carriers. Particularly preferred organic carriers are decane and dodecane.

Following each impregnation with the organosilicon compound, the catalyst is calcined at a rate of from about 0.2° C./minute to about 5° C./minute to a temperature greater than 200° C., but below the temperature at which the crystallinity of the molecular sieve is adversely affected. This calcination temperature will generally be below 600° C. and preferably is within the approximate range of 350 to 550° C. The duration of calcination at the calcination temperature may be from 1 to 24 hours, e.g., from 2 to 6 hours.

In addition to, or in place of, silica selectivation, the first catalyst component may be subjected to coke selectivation. This optional coke selectivation typically involves contacting the catalyst with a thermally decomposable organic compound at an elevated temperature in excess of the decomposition temperature of the compound, but below the temperature at which the crystallinity of the molecular sieve is adversely affected. This contact temperature may be, for example, less than about 650° C. Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. No. 4,117,026, incorporated by reference herein. By using a combination of silica selectivation followed by coke selectivation, the number of organosilicon impregnation treatments required to achieve a particular xylene diffusivity can be reduced.

Where the ethylbenzene conversion is effected by dealkylation, suitable conditions for the ethylbenzene conversion step include a temperature of about 350° C. to about 600° C., a pressure of about 10 kPa to about 30 kPa, a WHSV of about 3 to about 20, and a hydrogen to hydrocarbon mole ratio of about 0.5:1 to about 5.0:1.

In a second embodiment of the invention, the ethylbenzene conversion step is effected by isomerization so as to increase the overall xylene concentration in the feedstock. Ethylbenzene isomerization is a known process and can be conducted over a number of non-acidic or low acidity catalysts. Examples of suitable ethylbenzene isomerization catalysts include platinum on alumina, platinum-containing, potassium-exchanged zeolite L (including the zeolite-bound zeolite L disclosed in, for example, U.S. Pat. No. 6,040,259), platinum-containing mordenite, platinum-containing SAPO-11 (see, for example, U.S. Pat. No. 4,740,650) and platinum-containing titanosilicate ETS-10 (see, for example, U.S. Pat. No. 4,853,202). Other suitable catalysts include the MgAPSO materials, such as MgAPSO-31, as disclosed in U.S. Pat. Nos. 5,478,787 and 5,516,957 and platinum-exchanged, gallium-substituted ZSM-12 disclosed in U.S. Pat. Nos. 4,962,259 and 5,081,084. All the above patents are incorporated herein by reference.

Where the ethylbenzene conversion is effected by isomerization, suitable conditions for the ethylbenzene conversion step include a temperature of about 320° C. to about 440° C., a pressure of about 10 kPa to about 40 kPa, a WHSV of about 0.5 to about 15, and a hydrogen to hydrocarbon mole ratio of about 1.0:1 to about 6:1.

First Xylene Isomerization Catalyst

The first or main xylene isomerization catalyst may be selected from any of the catalysts conventionally employed for effecting xylene isomerization, but preferably is a molecular sieve having Constraint Index of about 1 to about 12 as discussed above in relation to ethylbenzene dealkylation catalysts. In particular, the first xylene isomerization catalyst is ZSM-5.

Other molecular sieves which can be used as the first xylene isomerization catalyst include, for example, zeolite Beta, MCM-22, synthetic and natural mordenite, synthetic and natural faujasite, and amorphous or ordered mesoporous materials, such as MCM-41 and MCM-48. Zeolite Beta is described in U.S. Pat. No. 3,308,069; MCM-22 in U.S. Pat. No. 4,954,325; Rare Earth X in U.S. Pat. No. 3,210,267; Rare Earth Y in U.S. Pat. No. 3,251,902 MCM-41 and MCM-48 in U.S. Pat. Nos. 5,098,684; 5,102,643; and 5,198,203; all incorporated by reference herein.

The acidity of the first xylene isomerization catalyst, expressed as the alpha value, may be less than about 150, e.g., less than about 100, e.g., at most 50, e.g., the alpha value may range from about 5 to about 25.

The first xylene isomerization catalyst preferably has an ortho-xylene sorption time of less than about 50 minutes and preferably less than about 10 minutes. This is typically achieved by using a small crystal size molecular sieve, for example a material having a crystal size, as determined by election microscopy, less than 1 micron and generally less than 0.5 micron, such as from about 0.02 to 0.05 micron.

The first reactor containing the first xylene isomerization catalyst and preferably the ethylbenzene conversion catalyst is operated under conditions effective to isomerize xylenes in the feed. Typical conditions include a temperature a temperature of about 350° C. to about 600° C., a pressure of about 1000 kPa to about 3000 kPa guage pressure, a WHSV of about 3 to about 20, and a hydrogen to hydrocarbon mole ratio of about 0.5:1 to about 5.0:1. More preferably, the conditions in the first reactor include a temperature of about 400° C. to about 450° C., a pressure of about 1400 kPa to about 1900 kPa, a WHSV of about 8 to about 12, and a hydrogen to hydrocarbon mole ratio of about 1.0 to about 2.0.

Second Xylene Isomerization Catalyst/Olefin Removal Catalyst

In addition to the first isomerization catalyst, the process of the present invention employs a second or trim isomerization catalyst contained in a second reactor which also accommodates a olefin removal catalyst, either as a mixture with the second isomerization catalyst or more preferably as a separate bed downstream of a bed of the second isomerization catalyst. Alternatively, a single catalyst capable of both isomerizing the xylenes in the feedstock and removing olefins from the feedstock may be employed as the second isomerization catalyst. In a preferred embodiment, the second reactor is a fixed bed reactor in which the xylene isomerization catalyst and olefin removal catalyst are in sequential beds, with the feedstock being cascaded between the beds without interstage separation. In a revamp of an existing xylene isomerization unit, the second reactor is preferably an existing clay treater.

Where the second reactor contains separate isomerization and olefin removal catalysts, the xylene isomerization component is preferably a molecular sieve selected from MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-49 being particularly preferred. The entire contents of the above references are incorporated by reference herein.

Alternatively, the xylene isomerization component can be one of the Constraint Index 1–12 molecular sieves described above as being suitable for use as the ethylbenzene dealkylation catalyst, in which case the molecular sieve is preferably ZSM-5.

In any event, the molecular sieve used as the xylene isomerization component should have a relatively high acid activity, since the conditions used the second reactor will generally be less severe than those conventionally employed in a xylene isomerization reactor. In particular, the xylene isomerization catalyst preferably has an alpha value greater than 300 and more preferably greater than 600.

The xylene isomerization catalyst preferably has an ortho-xylene sorption time of less than about 50 minutes and preferably less than about 10 minutes. This is typically achieved by using a small crystal size molecular sieve, having an average crystal size of 0.02–0.05 micron, as the active material of the catalyst.

Where separate isomerization and olefin removal catalysts are employed in the second reactor, the olefin removal catalyst can be a conventional clay catalyst or more preferably comprises a porous crystalline material having pores and/or surface pockets defined by a ring of ten or more tetrahedrally coordinated atoms. Examples of suitable porous crystalline materials for use as the olefin removal catalyst include ZSM-4 (U.S. Pat. No. 3,923,639), mordenite, ZSM-18 (U.S. Pat. No. 3,950,496), ZSM-20 (U.S. Pat. No. 3,972,983), zeolite beta (U.S. Pat. No. 3,308,069 and Re 28,341), faujasite, USY (U.S. Pat. No. 3,449,070), REY (U.S. Pat. No. 4,415,438), MCM-22, PSH-3, SSZ-25, MCM-36, MCM-49 and MCM-56. Other suitable olefin removal catalysts include the mesoporous crystalline materials M41S (U.S. Pat. No. 5,102,643). Preferably, the olefin removal catalyst comprises MCM-22. The entire contents of the above references are incorporated by reference herein.

Preferably, the olefin removal catalyst has an alpha value less than 100.

Alternatively, a single catalyst may be used to effect both xylene isomerization and olefin removal. A suitable single catalyst would be MCM-22, PSH-3, SSZ-25, MCM-36, MCM-49 or MCM-56, with MCM-22 being particularly preferred.

The conditions in the second reactor are selected so as to be effective to isomerize the xylenes in the feedstock as well as to remove olefins without excessive undesirable side reactions. In general, therefore the conditions will be less severe than those employed in the first reactor and in particular will be such as to maintain the feedstock at least partially in the liquid phase. Suitable conditions include conditions include a temperature of about 120 to about 260° C., a pressure of about 445 kPa to about 7600 kPa and a WHSV of about 0.1 to about 100. More preferably, the conditions include a temperature of about 150 to about 230°

C., a pressure of about 790 to about 3550 kPa and WHSV of about 1 to about 30. In general, the processes in the second reactor are conducted in the absence of added hydrogen.

The relative amounts of the first and second isomerization catalysts are not critical but in general the ratio of the first isomerization catalyst to the second isomerization catalyst will be about 0.5 to about 4.0 by weight, for example about 1.0 to about 2.0 by weight.

The present invention will be further illustrated by way of the following Example. Unless stated otherwise, all percentages, parts, etc. presented in the examples are by weight.

EXAMPLE

To trim isomerize a stream of equilibrium distributed mixed xylenes and ethylbenzene, as well as to remove olefins, a two-bed catalyst system was used in a single reactor. The top bed comprised a high activity, small crystal size ZSM-5 catalyst, whereas the bottom bed comprised a self-bound MCM-22 catalyst.

The ZSM-5 crystals used in the top bed had a $SiO_2:Al_2O_3$ ratio of approximately 16:1 and average crystal size of about 0.01 to 0.02 micron, and were synthesized in an autoclave. These crystals were heated under nitrogen to 482° C. and held at this temperature for 3 hours, then exchanged with 1.0 N $NH_4NO_3$ solution for one hour at room temperature. The crystals were then filtered, rinsed thoroughly with de-ionized water, and then dried in air at 120° C. The dried material was heated to 482° C. in a mixture of 5% $N_2$ and 95% air, held for 2 hours at 482° C., then heated to 538° C. in 100% air and held at 538° C. for six hours. The resulting material contained less than 500 ppm Na and had an alpha value of 880.

The self-bound MCM-22 catalyst used in the bottom bed was manufactured by first crystallizing the MCM-22 zeolite following established crystallization procedures. The MCM-22 zeolite was then formed into extrudates, in the absence of a binder, using known procedures. The extrudates were then calcined and the calcined extrudates were next contacted with an aqueous solution of ammonium ions to exchange alkali metal ions with intermediate ammonium ions. The exchanged catalyst was then calcined to provide the acidic hydrogen form. Self-bound MCM-22 has been measured to have an alpha value of 390.

Four grams of ZSM-5 catalyst were loaded into a ¾" outer diameter reactor on top of one gram of the MCM-22 catalyst. A layer of quartz wool separated the two catalyst beds. The reactor was liquid filled with the hydrocarbon feed and the pressure was raised to 1480 kPa (200 psig) before the temperature was raised to 260° C.

The feed was generated from an EB dealkylation-based xylene isomerization reactor that was operating at 413° C. Flow of the feed was set to 8 g/hr. The WHSV for the ZSM-5 bed was 2 $hr^{-1}$, while that for the MCM-22 bed was 8 $hr^{-1}$. Table 1 shows the xylenes distribution of the reactor feed and the product after six days of operation.

TABLE 1

| Xylene | Feed % | Product % |
| --- | --- | --- |
| PX/Xylene Selectivity | 23.7 | 23.9 |
| MX/Xylene Selectivity | 52.3 | 53.9 |
| OX/Xylene Selectivity | 24.0 | 22.2 |
| Bromine Index | 340 | 40 |

The equilibrium PX/Xylene selectivity at the temperature the feed was generated (413° C.) is 23.5% (based on a published equilibrium correlation). It is known in the art that concentrations of PX/Xylene can be slightly higher than published equilibrium selectivities. The equilibrium PX/Xylene selectivity at the temperature the experiment in Table 1 occurred (260° C.) is 24.0%. The favorable thermodynamics for the experiment in Table 1 caused an increase in the PX/Xylene concentration in the reactor effluent. This concentration was above that which was capable of being produced at the higher temperatures in the main isomerization reactor.

Table 1 also shows that the BI can be reduced by combining this trim isomerization catalyst with an olefin removal catalyst.

What is claimed is:

1. A process for isomerizing xylenes in a feed containing xylenes and olefins, said process comprises:
   (I) providing a first reactor containing a first isomerization catalyst;
   (II) providing a second reactor containing a second isomerization catalyst and a further catalyst effective for removing olefins contained in said feed;
   (III) wherein said process is carried out by either;
   (A)
      (i) contacting the feed with said first isomerization catalyst contained in said first reactor under a first set of conditions effective to isomerize xylenes in the feed; and
      (ii) contacting the product of step (A)(i) with said second isomerization catalyst in said second reactor under a second set of conditions, said second reactor being separate from said first reactor and said further catalyst effective to remove olefins in the product of step (A)(i); or
   (B)
      (i) contacting the feed with said second isomerization catalyst contained in said second reactor under a second set of conditions, said second reactor being separate from said first reactor and containing said further catalyst effective under said second set of conditions to remove olefins in the feed;
      (ii) contacting the product step of (B)(i) with said first isomerization catalyst contained in said first reactor under a first set of conditions effective to isomerize xylenes in the product of step (B)(i).

2. The process of claim 1, wherein the contacting the feed with the first isomerization catalyst occurs after contacting the xylenes with the second isomerization catalyst.

3. The process of claim 1, wherein the contacting the feed with the first isomerization catalyst occurs before contacting the feed with the second isomerization catalyst.

4. The process of claim 1 wherein the second set of conditions is different from the first set of conditions.

5. The process of claim 1 wherein the second set of conditions includes a lower temperature than the first set of conditions.

6. The process of claim 1, wherein the conditions in the first reactor include a temperature of about 350° C. to about 600° C., a pressure of about 10 kPa to about 30 kPa, a WHSV of about 3 to about 20, and a hydrogen to hydrocarbon mole ratio of about 0.5:1 to about 5.0:1.

7. The process of claim 1, wherein the conditions in the first reactor include a temperature about 400° C. to about 450° C., a pressure of about 1400 kPa to about 1900 kPa, a WHSV of about 8 to about 12, and a hydrogen to hydrocarbon mole ratio of about 1.0 to about 2.0.

8. The process of claim 1, wherein the conditions in the second reactor include a temperature of about 120° C. to about 260° C., a pressure of about 445 kPa to about 7000 kPa and a WHSV of about 0.1 to about 100.

9. The process of claim 1, wherein the conditions in the first reactor include a temperature about 150° C. to about 230° C., a pressure of about 790 kPa to about 3550 kPa, and a WHSV of about 1 to about 30.

10. The process of claim 1, wherein the first isomerization catalyst includes a molecular sieve having a Constraint Index of about 1 to about 12.

11. The process of claim 1, wherein the first isomerization catalyst includes ZSM-5.

12. The process of claim 1, wherein the second isomerization catalyst includes a molecular sieve having a Constraint Index of about 1 to about 12.

13. The process of claim 1, wherein the second isomerization catalyst includes a molecular sieve selected from the group consisting of ZSM-5, MCM-22, PSH-3, SSZ-25, MCM-36, MCM-49 and MCM-56.

14. The process of claim 1, wherein the second isomerization catalyst has an alpha value greater than 300.

15. The process of claim 1 wherein the weight ratio of the first isomerization catalyst to the second isomerization catalyst is about 0.5 to about 4.0.

16. The process of claim 1 wherein the weight ratio of the first isomerization catalyst to the second isomerization catalyst is about 1.0 to about 2.0.

17. The process of claim 1, wherein the further catalyst is selected from the group consisting of clay, ZSM-4, mordenite, ZSM-18, ZSM-20, zeolite beta, faujasite, USY, REY, MCM-22, PSH-3, SSZ-25, MCM-36, MCM-49 and MCM-56.

18. The process of claim 1, wherein the further catalyst comprises MCM-22.

19. The process of claim 1, wherein the further catalyst has an alpha value less than 100.

20. A process for isomerizing xylenes in a feed which contains ethylbenzene, xylenes, and olefins, which process comprises the steps of:

(I) providing a first reactor containing a first isomerization catalyst;

(II) providing a second reactor containing a second isomerization catalyst and a further catalyst effective for removing olefins contained in said feed;

(III) wherein said process is carried out by either;

(A)(i) contacting the feed with an ethylbenzene conversion catalyst under ethylbenzene conversion conditions, wherein the ethylbenzene conversion catalyst is effective under the ethylbenzene conversion conditions to convert ethylbenzene in the feed and produce an ethylbenzene-depleted product;

(ii) contacting said ethylbenzene-depleted product with a said first isomerization catalyst in said first reactor under a first set of conditions effective to isomerize xylenes in said ethylbenzene-depleted product to produce an isomerized product; and (iii) contacting the isomerized product of step (A)(ii) with said second isomerization catalyst in said second reactor under a second set of conditions effective to isomerize xylenes in said product the second reactor also containing said further catalyst effective under said second set of conditions to remove olefins in said isomerized product; or (B)(i) contacting the feed with an ethylbenzene conversion catalyst under ethylbenzene conversion conditions, wherein the ethylbenzene conversion catalyst is effective under the ethylbenzene conversion conditions to convert ethylbenzene in the feed and produce an ethylbenzene-depleted product:

(ii) contacting said ethylbenzene-depleted product with said second isomerization catalyst in said second reactor under a second set of conditions effective to isomerize xylenes in said product, the second reactor also containing said further catalyst to remove olefins in said ethylbenzene-depleted product, and (iii) contacting the product of step (B)(ii) with said first isomerization catalyst in said first reactor under a first set of conditions effective to isomerize xylenes in said product to produce an isomerized product.

21. The process of claim 20, wherein the ethylbenzene conversion catalyst converts ethylbenzene primarily by dealkylation.

22. The process of claim 21, wherein the ethylbenzene conversion catalyst comprises an intermediate pore molecular sieve having a Constraint Index of about 1 to about 12.

23. The process of claim 22, wherein the molecular sieve is selected from ZSM-5; ZSM-11; ZSM-12; ZSM-22; ZSM-23; ZSM-35; ZSM-48, ZSM-57; or ZSM-58.

24. The process of claim 20, wherein the ethylbenzene conversion catalyst converts ethylbenzene primarily by isomerization to xylenes.

25. The process of claim 24, wherein the ethylbenzene conversion catalyst is platinum on alumina, platinum-containing, potassium-exchanged zeolite L, platinum-containing mordenite, platinum-containing SAPO-11 or platinum-containing ETS-10.

26. The process of claim 20, wherein the ethylbenzene conversion catalyst is located in the first reactor.

27. The process of claim 20, wherein the ethylbenzene conversion catalyst is located in a third reactor upstream of the first and second reactors.

* * * * *